United States Patent
Berger et al.

(10) Patent No.: US 11,141,353 B2
(45) Date of Patent: Oct. 12, 2021

(54) FLOWABLE COMPOSITION

(71) Applicant: DENTSPLY SIRONA Inc., York, PA (US)

(72) Inventors: Todd Patrick Berger, Owasso, OK (US); Adam Zachary Baratz, Jenks, OK (US); Sheridan Lynn Rose, Scapula, OK (US)

(73) Assignee: DENTSPLY SIRONA INC., York, PA (US)

( * ) Notice: Subject to any disclaimer, the term of this patent is extended or adjusted under 35 U.S.C. 154(b) by 300 days.

(21) Appl. No.: 15/996,671

(22) Filed: Jun. 4, 2018

(65) Prior Publication Data

US 2018/0344580 A1    Dec. 6, 2018

Related U.S. Application Data

(60) Provisional application No. 62/515,906, filed on Jun. 6, 2017.

(51) Int. Cl.
| | | |
|---|---|---|
| *A61K 6/54* | (2020.01) | |
| *A61K 6/56* | (2020.01) | |
| *A61K 6/851* | (2020.01) | |
| *A61K 6/887* | (2020.01) | |
| *A61K 6/896* | (2020.01) | |
| *A61K 6/17* | (2020.01) | |

(52) U.S. Cl.
CPC ............... *A61K 6/54* (2020.01); *A61K 6/56* (2020.01); *A61K 6/851* (2020.01); *A61K 6/887* (2020.01); *A61K 6/896* (2020.01); *A61K 6/17* (2020.01)

(58) Field of Classification Search
CPC . A61K 6/54; A61K 6/71; A61K 6/887; A61K 6/896; A61K 6/56; A61K 6/17
See application file for complete search history.

(56) References Cited

U.S. PATENT DOCUMENTS

| | | | |
|---|---|---|---|
| 4,813,876 A * | 3/1989 | Wang | ................ A61K 6/54 433/224 |
| 5,415,547 A | 5/1995 | Mahmoud | |
| 5,769,638 A | 6/1998 | Mahmoud | |
| 7,892,342 B2 | 2/2011 | Primus | |
| 8,658,712 B2 | 2/2014 | Primus | |
| 9,351,909 B2 | 5/2016 | Berger | |
| 2007/0077538 A1* | 4/2007 | Musikant | ................ A61K 6/54 433/224 |

FOREIGN PATENT DOCUMENTS

| | | |
|---|---|---|
| EP | 2638892 A1 | 9/2013 |
| WO | 2005087178 A1 | 9/2005 |
| WO | WO 2005/087178 * | 9/2005 |
| WO | 2008008184 A2 | 1/2008 |

OTHER PUBLICATIONS

Written Opinion of the International Searching Authority; PCT/US2018/035789; Sep. 20, 2018 (completed); dated Sep. 27, 2018 (mailed).

International Search Report; PCT/US2018/035789; Sep. 20, 2018 (completed); dated Sep. 27, 2018 (mailed).

* cited by examiner

*Primary Examiner* — C Melissa Koslow
(74) *Attorney, Agent, or Firm* — Dentsply Sirona Inc.

(57) ABSTRACT

A dental composition comprising a pre-reacted particulate mineral trioxide aggregate (MTA) dispersed in a polymer matrix wherein the content of MTA in the composition is in the range of 20 to 50 percent by weight based on the total weight of the composition.

11 Claims, No Drawings

FLOWABLE COMPOSITION

RELATED APPLICATIONS

This patent application claims the benefit of and priority to U.S. Provisional Application Ser. No. 62/515,906, filed on Jun. 6, 2017, which is herein incorporated by reference for all purposes.

FIELD OF INVENTION

The present invention relates to the field of endodontics, more particularly obturation materials for endodontics.

BACKGROUND OF THE INVENTION

The present invention relates to an endodontic obturation material. Generic obturation materials are known from the prior art, such as Dentsply Sirona's proprietary ProRoot obturation material. ProRoot may be based on a reactive mineral trioxide aggregate (MTA) composition, which was marketed successfully over many years in the past given inter alia the ability of the unreacted MTA to stimulate regeneration of dental tissue.

However, reactive mineral trioxide aggregate (MTA) compositions generally require activation by mixing with a liquid prior to application into the root canal. Given that the time-consuming mixing step cannot be avoided, the handling of the material has always been the main problem of reactive mineral trioxide aggregate (MTA) compositions. Moreover, given that observing optimum mixing conditions may be essential for the success of the endodontic treatment, errors or variations on the part of the practitioner may be detrimental to the quality of the obturation.

Therefore, a need exists to provide an improved dental obturation material, which has significantly improved handling properties while at the same time maintaining any advantages of reactive mineral trioxide aggregate (MTA) compositions including the ability to stimulate regeneration of dental tissue.

SUMMARY OF THE INVENTION

The present disclosure provides compositions for improving handling properties of existing endodontic reactive mineral trioxide aggregate (MTA) compositions.

In a first aspect, the present invention may provide a dental composition comprising a pre-reacted particulate mineral trioxide aggregate (MTA) dispersed in a polymer matrix wherein the content of MTA in the composition is in the range of 20 to 50 percent by weight based on the total weight of the composition.

In another aspect, the present invention may provide a process for the preparation of a dental composition comprising the steps of: (i) curing an MTA composition; (ii) milling the cured MTA to an average particle size of from 0.1 to 100 microns for obtaining a particulate cured MTA; and (iii) dispersing the particulate cured MTA in a non-aqueous polymer matrix for forming a composite composition.

In yet another aspect, any of the aspects of the present invention may be further characterized by one or any combination of the following features: wherein the polymer matrix includes chemically cross-linked or crystalline polymers; wherein the polymer matrix includes a silicone and/or at least one hydrocarbon polymer; wherein the pre-reacted particulate MTA has an average particle size of from 0.1 to 100 microns; wherein the polymer matrix is present in an amount of 10 to 90 percent by weight based on the total weight of the composition; a dental composition for use in an endodontic treatment of a tooth; wherein the endodontic treatment is selected from the group consisting of root-end filling, apical plug for apexification, repair of root perforations, internal resorption, indirect pulp capping, direct pulp capping, obturation, and sealing the root canal; wherein the dental composition is bio inductive for cementum; wherein the dental composition stimulates a hard tissue covering where a blood supply exists (apical foramen, interface with healthy pulp) thereby regenerating cementum which may if needed create a biological seal; wherein the dental composition does not stimulate an inflammatory process; wherein the dental composition supports tissue regeneration; wherein the dental composition is biocompatible with pulp and periradicular tissues; wherein the dental composition is not cytotoxic in the set or unset state; wherein the dental composition is antibacterial and/or antimicrobial due to a pH increase; wherein the dental composition produces hydroxyapatite when exposed to either blood or simulated body fluid; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

DETAILED DESCRIPTION OF THE INVENTION

The present invention focuses on the recognition that dental cements such as mineral trioxide aggregate's (MTA) (e.g., ProRoot® MTA) may include the ability to stimulate regeneration of dental tissue based on the presence of calcium ions on the surface of the material. Moreover, the present invention provides further recognition that pre-reacted MTA may be provided as a dental composition wherein calcium ions are present on the surface of MTA in an amount that the ability to stimulate regeneration of dental tissue may be maintained. Therefore, the present invention provides a flowable two part dental composition (Part A and Part B) where both Part A and Part B may include cured dental cement particles.

In one specific example, cured mineral trioxide aggregate (MTA) and/or cured dental cement particles may be provided in the present invention. Useful MTAs and/or cured dental cements are disclosed in U.S. Pat. Nos. 5,415,547, 5,769,638, 7,892,342, and 8,658,712, which are herein incorporated by reference for all purposes. Generally, a particulate material including the cement (Portland cement, alborg cement, and/or otherwise) and optionally a radiopacifier (e.g., bismuth oxide, calcium sulfate, ZrO2, calcium tungstate, and/or otherwise), and optionally Hydroxyapitite may be mixed with a liquid (e.g., water, SODIUM LAURYL SULFATE, POLYVINYL PYRROLIDONE, POLYVINYL ALCOHOL, PLASDONE K90, SODIUM CHLORIDE, POTASSIUM CHLORIDE, POTASSIUM DIHYDROGEN PHOSPHATE, DISODIUM PHOSPHATE, and otherwise, and mixtures thereof) and to form a dental cement composition.

Once the dental cement composition has cured (e.g., from 1 minute to 5 hours, preferably 1 minute to two hours, and more preferably from 1 minute to 30 minutes, the cured dental cement may then be reduced to particles to form cured dental cement particles ranging from 0.1 to 100 microns.

The present invention may include at least one polymerizable material. Desirably, the polymerizable material may include a liquid polyisoprene (e.g., methacrylated polyisoprene). The first polymerizable material may typically be present in an amount of at least about 1%, preferably at least about 5%, and more preferable at least about 10% by wt polymerizable material. Furthermore, it is appreciated that the first polymerizable material may typically be present in an amount of less than about 99%, preferably less than about 75% and preferably less than about 50% by wt the overall composition. For example, the first polymerizable material may typically be present in an amount ranging from about 1% to about 99%, preferably from about 5% to about 75%, and more preferably from about 10% to about 50% by wt the overall composition.

Examples of polymerizable compounds (e.g., liquid polyisoprene copolymers) that may be used in the composition of this invention, include, but are not limited to, cyclic compounds that are capable of undergoing a ring opening reaction such as epoxy modified liquid polyisoprene compounds (e.g., difunctional and multifunctional epoxy modified liquid polyisoprene compounds) and ring opening nucleophiles such as amine modified liquid polyisoprene compounds (e.g., aminoalkylfunctional liquid Polyisoprene). Most preferred modified liquid polyisoprene are novel. The methacylate polyisoprene can be purchased from Kuraray Co., Ltd.

The present invention may further include at least one initiating component. In one specific example, it is contemplated that the crosslinking reaction may occur through the use of an amine and peroxide, though not required. Optionally, the curing agent may further include an accelerant. One preferred alcohol may be a peroxide or a pentanol. Peroxides may include Hydrogen peroxide, BPO (Luperox® A98, Benzoyl peroxide). Others viable peroxides are contemplated.

One preferred amine may include an aromatic diamine such as m-Phenylenediamine (MPD), o-Phenylenediamine (OPD), and p-Phenylenediamine (PDP), however, other amines and/or diamines may be utilized. Optionally, energy sources such as heat, light (UV and/or IR), or otherwise may be utilized in place of the amine component to effectuate the crosslinking with the peroxide.

It is believed that the "accelerant" dries the cured surface and over comes oxygen inhibition. One preferred accelerant may include HEMA (2-Hydroxyethyl methacrylate) however, Glycidyl methacrylate (2,3-Epoxypropyl methacrylate) or Lauryl methacrylate (Dodecyl methacrylate) may be viable substitutes for the accelerant as well.

The composition may include one or more fillers. Fillers having Radiopacity useful in accordance with the invention, without limitation, include inorganic fillers such as Ag, $TiO_2$, $La_2O_3$, $ZrO_2$, $BaSO_4$, $CaWO_4$, $BaWO_4$, $Fe_2O_3$ and $Bi_2O_3$, $CeO_2$, MgO, ZnO, W, $WO_3$, lanthanide salts, polymer granulates, barium or strontium-containing glass. The glass may contain fluoride for fluoride release in vivo. When included, the radiopacifier may be present in an amount of at least about 20%, preferably at least about 30%, and more preferable at least about 40% by wt the overall composition. Furthermore, the radiopacifier may be present in an amount of less than about 80%, preferably less than about 70% and preferably less than about 60% by wt the overall powder filler composition. For example, the radiopacifier may be present in an amount ranging from about 20% to about 80%, preferably from about 30% to about 70%, and more preferably from about 40% to about 60% by wt the overall composition. When included, the radiopacifier may present an include at least three radiopacifier materials. In one specific example, the at least three radiopacifiers include from about 20 to about 70% $CaWO_4$, from about 30 to about 50% $CaWO_4$ and from about 35 to about 45% $CaWO_4$.

Other fillers that may be employed include, but are not limited to silicas, aluminas, magnesias, titanias, inorganic salts, metallic oxides, (e.g., zinc oxides, silicon dioxide, calcium hydroxide, or otherwise), bioglass, mineral trioxide aggregate and glasses, though not required. Other filler material may be present in an amount of at least about 0.1%, preferably at least about 1%, and more preferably at least about 5% by wt the overall powder filler composition. Furthermore, the other filler material may be present in an amount of less than about 25%, preferably less than about 20% and more preferably less than about 15% by wt the overall powder filler composition. For example, the other filler material may be present in an amount ranging from about 0.1% to about 25%, preferably from about 0.5% to about 20%, and more preferably from about 1% to about 10% by wt the overall composition.

| Ingredient | A side (wt %) | B side (wt %) |
|---|---|---|
| Polymerizable Material | 5-35 (preferable) 10-30 (more preferable) 15-25 (most preferable) | 5-35 (preferable) 10-30 (more preferable) 15-25 (most preferable) |
| Initiating Component (e.g., Peroxide) | 1-20 (preferable) 3-15 (more preferable) 5-10 (most preferable) | 0-20 (preferable) |
| Amine | 0-20 (preferable) | 1-20 (preferable) 2-15 (more preferable) 4-10 (most preferable) |
| Accelerator | 1-20 (preferable) 3-15 (more preferable) 5-10 (most preferable) | 1-20 (preferable) 3-15 (more preferable) 5-10 (most preferable) |
| Radiopacifier | 15-75 (preferable) 20-60 (more preferable) 30-50 (most preferable) | 15-75 (preferable) 20-60 (more preferable) 30-50 (most preferable) |
| Thickener | 0.05-20 (preferable) 0.5-10 (more preferable) 1-8 (most preferable) | 0.05-20 (preferable) 0.5-10 (more preferable) 1-8 (most preferable) |
| Cured dental cement particles (e.g., cured ProRoot MTA particles) | 5-35 (preferable) 10-30 (more preferable) 15-25 (most preferable) | 5-35 (preferable) 10-30 (more preferable) 15-25 (most preferable) |
| Total | 100.0 | 100.0 |

The ProRoot MTA may be a place holder for other formulations of set MTA particles. In one specific formulation; ProRoot MTA may be Aalborg cement mixed with water in a Powder: Liquid ratio of 3:1. The liquid in this scenario would be deionized water. Deionized water may be the preferred purified water. Deionized water 'has had almost all of its mineral ions removed, such as cations like sodium, calcium, iron, and copper, and anions such as chloride and sulfate.' Once the ProRoot MTA (as described above) may be mixed into the compound the ions on the surface are picked up into the deionized water. It may be these ions which are an important part of the healing and regeneration produced by the ProRoot MTA.

The grade of Silicon Dioxide may be chosen so it has the smallest possible hydrophobicity. The preferred grade of Silicon Dioxide may be Aerosil 200 Pharma fumed silica. This formulation could also include tocopherol, which may be a water insoluble viscous liquid with known anti-inflammatory properties.

MTA, by itself, may be not known to be retreatable. However, when the MTA may be in a polymer matrix in the form of ground particles, it reacts just like any other filler. Gutta-percha may be widely known to be retreatable, and gutta-percha with MTA particles in it does not change that. This would also apply to a silicone polymer matrix, as mentioned in the ROI.

Hardened (cured or partially cured) MTA particles may be provided having various particle sizes in a range from about 100 nm to about 500 μm. Typically, hardened MTA particles may be provided having various particle sizes in an amount greater than about 25 microns, and preferably greater than about 40 microns. Furthermore, hardened MTA particles may be provided having various particle sizes in an amount less than about 225 microns, and preferably less than about 200 microns. For example, hardened MTA particles may be provided having various particle sizes in an amount ranging from about 25 microns to about 200 microns, and preferably from about 40 microns to about 200 microns.

These hardened MTA particles could also be different morphologies (spherical, platelet, linear, granular). These different particles could be obtained using various grinding operations (vortex, cryogenic, ball mill, impact, high pressure grinding rolls, planetary ring-roller mill). These different morphologies and grinding procedures will provide different properties to the dental compounds. The hardened MTA particles will comprise 1 to 50% of the dental compounds.

It is appreciated that two or more different hardened MTA particles may be provided, though not required. In one specific example, a dental composition may be provided having a first cured MTA material with various particle sizes ranging from about 25 microns to about 75 microns and a second cured MTA material (being different from the first cured MTA material) with various particle sizes ranging from about 150 microns to about 225 microns.

The present invention may provide a process for the preparation of the dental compositions. The process may include the steps of: providing an MTA composition; at least partially curing the MTA composition; milling the at least partially cured MTA composition to an average particle size of from 0.1 to 500 μm for obtaining a particulate hardened MTA; and dispersing the particulate hardened MTA in a non-aqueous matrix for forming a dental compound. Preferably, the MTA composition is fully cured prior to the milling step, though not required.

The matrix for these compounds may be silicone polymer, resin, and/or gutta-percha. These compounds may include other additives (radiopacifiers, thickening agents, thinning agents, colorants). These dental compounds may be for use in the endodontic treatment of a tooth. More specifically, Root-End Filling, Apical Plug for Apexification, Repair of Root Perforations, Internal Resorption, Indirect Pulp Capping, Direct Pulp Capping, Obturation, Sealing Root Canal.

Workers skilled in the art will appreciate that various modifications can be made to the illustrated embodiments and description herein without departing from the spirit and scope of the present invention. It is intended that all such modifications within the spirit and scope of the present invention be covered by the appended claims. The term "about" means plus or minus 5 percent of the specified value, preferably plus or minus 3 percent of the specified value, more preferably plus or minus 1 percent of the specified value.

The invention claimed is:

1. A dental composition comprising a pre-reacted particulate of cured mineral trioxide aggregate (MTA) dispersed in a non-aqueous polymer matrix, wherein the content of cured particulate MTA is in the range of 20 to 50 by weight based on the total weight of the composition and wherein the pre-reacted particulate of cured MTA has an average particle size of from 0.1 to 100 microns; wherein the non-aqueous polymer matrix includes a silicone polymer or a polymerizable material selected from methacrylated polyisoprene, epoxy modified liquid polyisoprene or amine modified liquid polyisoprene.

2. The dental composition according to claim 1, wherein the polymer matrix is present in an amount of 10 to 90 percent by weight based on the total weight of the composition.

3. The dental composition according to claim 1, for use in endodontic treatment of a tooth.

4. The dental composition for use in the according to claim 3, wherein the endodontic treatment is selected from the group consisting of root-end filling, apical plug for apexification, repair of root perforations, internal resorption, indirect pulp capping, direct pulp capping, obturation, and sealing the root canal.

5. The dental composition according to claim 1, wherein the dental composition:
   (i) is bio inductive for cementum;
   (ii) stimulates a hard tissue covering where a blood supply exists thereby regenerating cementum creates a biological seal;
   (iii) does not stimulate an inflammatory process,
   (iv) supports tissue regeneration;
   (v) is biocompatible with pulp and periradicular tissues; and/or
   (vi) is not cytotoxic in the set or unset state.

6. The dental composition according to claim 1, wherein the dental composition is antibacterial and/or antimicrobial due to a pH increase.

7. The dental composition according, to claim 1, wherein the dental composition produces hydroxyapatite when exposed to either blood or simulated body fluid.

8. A process for the preparation of a dental composition comprising the steps of:
   (i) providing a cured mineral trioxide aggregate MTA;
   (ii) milling the cured MTA to an average particle size of from 0.1 to 100 microns to form a pre-reacted particulate of cured MTA;
   (iii) dispersing the pre-reacted particulate of cured MTA in a non-aqueous polymer matrix for forming a composite composition; wherein the non-aqueous polymer matrix includes a silicone polymer or a polymerizable material selected from methacrylated polyisoprene, epoxy modified liquid polyisoprene or amine modified liquid polyisoprene.

9. The process according to claim 8, wherein the dental composition:
(i) is bio inductive for cementum;
(ii) stimulates a hard tissue covering where a blood supply exists thereby regenerating cementum creates a biological seal;
(iii) does not stimulate an inflammatory process;
(iv) supports tissue regeneration;
(v) is biocompatible with pulp and periradicular tissues; and/or
(vi) is not cytotoxic in the set or unset state.

10. The process according to claim 8, wherein the dental composition is antibacterial and/or antimicrobial due to a pH increase.

11. The process according to claim 8, wherein the dental composition produces hydroxyapatite when exposed to either blood or simulated body fluid.

* * * * *